US005708015A

United States Patent [19]
Garst et al.

[11] Patent Number: 5,708,015
[45] Date of Patent: Jan. 13, 1998

[54] METHOD FOR USING PHARMACEUTICAL COMPOSITIONS CONTAINING 2-(2-ALKYPHENYL-AMINO)-THIAZOLINES AS ADRENERGIC AGENTS

[75] Inventors: Michael E. Garst, Newport Beach; James E. Burke, Tustin; Larry A. Wheeler, Irvine, all of Calif.

[73] Assignee: Allergan, Waco, Tex.

[21] Appl. No.: 739,232

[22] Filed: Oct. 29, 1996

Related U.S. Application Data

[62] Division of Ser. No. 141,143, Oct. 22, 1993, Pat. No. 5,580,892.
[51] Int. Cl.$^6$ ............................................. A61K 31/425
[52] U.S. Cl. ................................................. 514/370
[58] Field of Search ..................................... 514/370

[56] References Cited

U.S. PATENT DOCUMENTS

| | | | |
|---|---|---|---|
| 2,027,030 | 1/1936 | Englemann et al. | 260/44 |
| 2,876,232 | 3/1959 | Bloom | 260/307 |
| 3,432,600 | 3/1969 | Harvey, Jr. et al. | 424/273 |
| 3,453,284 | 7/1969 | Harvey, Jr. et al. | 260/307 |
| 3,598,833 | 8/1971 | Hiltmann et al. | 260/307 |
| 3,624,092 | 11/1971 | Levitt et al. | 260/288 |
| 3,636,219 | 1/1972 | Culik et al. | 514/190 |
| 3,679,798 | 7/1972 | Culik et al. | 424/265 |
| 3,890,319 | 6/1975 | Danielewicz et al. | 260/250 |
| 3,907,996 | 9/1975 | Griss et al. | 424/270 |
| 3,993,766 | 11/1976 | Behner et al. | 424/270 |
| 4,256,755 | 3/1981 | Smith, Jr. | 424/272 |
| 4,515,800 | 5/1985 | Cavero et al. | 514/392 |
| 4,587,257 | 5/1986 | DeSantis et al. | 514/392 |
| 4,683,229 | 7/1987 | Demarinis et al. | 514/213 |
| 5,066,664 | 11/1991 | Gluchowski | 514/377 |
| 5,091,152 | 2/1992 | Gluchowski | 544/105 |
| 5,151,440 | 9/1992 | Gluchowski | 514/377 |
| 5,180,721 | 1/1993 | Burke | 514/213 |
| 5,252,595 | 10/1993 | Gluchowski | 514/392 |
| 5,580,892 | 12/1996 | Garst et al. | 514/377 |

FOREIGN PATENT DOCUMENTS

| | | |
|---|---|---|
| 0251453 | 1/1988 | European Pat. Off. |
| 1191381 | 6/1963 | Germany . |
| 1195323 | 6/1963 | Germany . |
| 2127267 | 2/1971 | Germany . |
| 58-46092 | of 1983 | Japan . |

OTHER PUBLICATIONS

Wollweber et al. Chem. Abstr., vol. 70, entry 47428f (1969) abstracting GB 1 132 409.
"Heteroaromatic Analogues of the alpha$_2$-Adrenoreceptor Partial Agonist Clonidine" *J. Med. Chem.*, 1989, 32, 1627–1630, Chapleo et al.

"Possible Subdivision of Postsynaptic x-Adrenoceptors Mediating Pressor Responses in the Pithed Rat", Nauyn-Schmiedeberg's Archives of Pharmacology, 310, 189–193, (1979) Timmermans, et al.

"Pharmacologic Differentiation Between Pre-and Postjunctional x$_2$-adrenoceptors by SK & F 104078", Nauyn-Schmiedeberg's Archives of Pharmacology, 336, 415–418, (1987) Ruffolo, R., et al.

"Distribution and Function of Pheripheral—Adrenoceptors in the Cardiovascular System", Pharmacology Biochemistry & Behavior, 22, 827–833, (1985) Ruffolo, R.

"Clonidine and Related Analogues. Quantitative Correlations", *Journal of Medicinal Chemistry*, vol., 19, No. 8, pp. 1049–1053, (1976) B. Rouot, et al.

K. Darmsataphorn et al., Gastroenterology, v.86, No. 1, 1984, 120–128.

*Primary Examiner*—José G. Dees
*Assistant Examiner*—Mary C. Cebulak
*Attorney, Agent, or Firm*—Gabor L. Szekeres; Robert J. Baran; Martin A. Voet

[57] ABSTRACT

A pharmaceutical composition, useful for treating animals of the mammalian species, including humans, to treat diseases and conditions which normally respond to treatment with alpha$_2$ adrenergic agents, contains as its active alpha$_2$ adrenergic agent ingredient one or more compounds of the formula

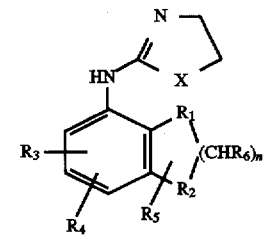

where X is O, S or NH; n is an integer with the values of 0, 1 or 2; when n is 0 then R$_1$ is lower alkyl having 1 to 6 carbon atoms and R$_2$ is H or lower alkyl having 1 to 6 carbon atoms; when n is 1 or 2, then R$_1$ and R$_2$ both are methylene (CH$_2$), or methylene substituted with an R$_5$ group where R$_5$ is lower alkyl of 1 to 6 carbons; R$_3$ and R$_4$ independently are H or lower alkyl having 1 to 6 carbons; R$_6$ is H or lower alkyl of 1 to 6 carbons.

6 Claims, No Drawings

METHOD FOR USING PHARMACEUTICAL COMPOSITIONS CONTAINING 2-(2-ALKYPHENYL-AMINO)-THIAZOLINES AS ADRENERGIC AGENTS

CROSS-REFERENCE TO RELATED APPLICATION

The present application is a divisional of application Ser. No. 08/141,143, filed on Oct. 22, 1993, to be issued as U.S. Pat. No. 5,580,892.

BACKGROUND OF THE INVENTION

1. Field of the Invention

The present invention is directed to pharmaceutical compositions which have adrenergic effects, and which comprise as active ingredients one or more 2-(2-alkyl-phenylamino)-oxazoline, 2-(2-alkylphenylamino)-thiazoline or 2-(2-alkylphenylamino)imidazoline compounds. The pharmaceutical compositions are useful for treating or preventing conditions in animals of the mammalian species which normally respond to treatment by adrenergic agents. Thus, the pharmaceutical compositions of the inventions are useful as agents for altering the rate of fluid flow in the gastrointestinal tract (anti-diarrhetic), anti-spastic, anti-hypertensive, anti-ischemic, anti-epileptic, agents for increasing fluid flow in at least one kidney (diuretic) anesthetic, memory-enhancing agents and as sleeping aids. In another aspect, the present invention is directed to administering such formulations and compositions to animals of the mammalian species (including humans) for treating the above-noted diseases and conditions. 2. Brief Description of Background Art Adrenergic agents, and particularly agents affective on $\alpha_2$ adrenergic receptors are known in the art. For example, U.S. Pat. No. 5,091,528 describes 6- or 7-(2-imino-2-imidazolidine)-1,4-benzoxazines as $\alpha$ adrenergic agents. Published European Patent Application 0 251 453 describes certain cyclohexyl substituted amino-dihydrooxazoles, -thiazoles and -imidazoles as $\alpha_2$ adrenergic agents. U.S. Pat. No. 3,598,833 describes 2-cycloalkylamino oxazolines having local anesthetic, sedative, vasoconstrictory, mucous membrane deswelling, blood pressure depressant and gastric fluid secretion inhibitory effects. Further United States and foreign patents and scientific publications which pertain to substituted amino-oxazolines, imidazolines and thiazolines are as follows:

U.S. Pat. No. 4,587,257 [2-(trisubstituted phenylimino) imidazoline compounds capable of controlling ocular bleeding];

U.S. Pat. No. 3,636,219 [2-(substituted-phenylamino)-thiazolines and imidazolines having anticholinergic activity];

U.S. Pat. No. 3,453,284 [2-(substituted-anilino)-2-oxazolines;

U.S. Pat. No. 3,432,600 [partially reduced 2-(naphtylamino) oxazolines and indanylamino oxazolines;

U.S. Pat. No. 3,679,798 [compositions comprising arylaminooxazolines and an antocholigeneric agent];

U.S. Pat. No. 3,624,092 [amino-oxazolines useful as central nervous system depressants];

U.S. Pat. No. 2,876,232 [2-(9-fluorenylamino)-oxazolines,) and German Patent Nos. 1,191,381 and 1,195,323, and European Patent Application No. 87304019.0.

U.S. Pat. No. 4,515,800 [2-(trisubstituted phenylimino) imidazoline compounds, also known as 2-(trisubstituted-anilino)-1,3-diazacyclopentene-(2) compounds, treatment of glaucoma].

U.S. Pat. No. 5,066,664 [2-(hydroxy-2-alkylphenylamino)-oxazolines and thiazolines, anti-glaucoma and vasoconstrictive agents].

Chapleo et al. in Journal of Medicinal Chemistry, 1989 32, 1627–1630 describe heteroaromatic analogues of clonidine as partial agonists of $\alpha_2$ adrenoreceptor.

U.S. Pat. No. 5,151,440 describes ophthalmic compositions suitable for lowering intraocular pressure, comprising compounds of substantially the same structure as the compounds used as adrenergic agents in the present invention.

As it will become apparent from the ensuing description, some of the "composition of matter" used in the novel pharmaceutical compositions and methods of administration of the present invention are described or mentioned in one or more of the above-listed references, but the activity of these compounds as adrenergic agents, and especially as agents acting on the $\alpha_2$ adrenergic receptor is believed to be novel to the present invention.

SUMMARY OF THE INVENTION

The present invention covers pharmaceutical compositions, which comprise as active $\alpha_2$ adrenergic agents one or more compounds having the formula

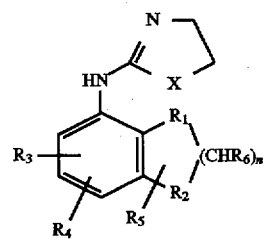

FORMULA 1 where X is , O, S or NH; n is an integer with the values of 0, 1 or 2; when n is 0 then $R_1$ is lower alkyl having 1 to 6 carbon atoms and $R_2$ is H or lower alkyl having 1 to 6 carbon atoms; when n is 1 or 2, then $R_1$ and $R_2$ both are methylene ($CH_2$), or methylene substituted with an $R_5$ group where $R_5$ is lower alkyl of 1 to 6 carbons; $R_3$ and $R_4$ independently are H or lower alkyl having 1 to 6 carbons; $R_6$ is H or lower alkyl of 1 to 6 carbons. The pharmaceutical compositions, containing one or more of the above-defined compounds as active ingredients, are administered to animals of the mammalian species for the purpose of treating or preventing one or more of the diseases or conditions which are known to respond to $\alpha_2$ adrenergic agents. Thus, the pharmaceutical compositions of the invention are administered to animals of the mammalian species, including humans, as agents for altering the rate of fluid transport in the gastrointestinal tract (anti-diarrhetic), as anti-spastic, anti-hypertensive, anti-ischemic, anti-epileptic agents, as agents for increasing renal fluid flow in at least one kidney (diuretic), as anesthetic, or memory-enhancing agents and as sleeping aids.

General Embodiments

Definitions

The term "alkyl" as used here refers to and includes normal and branch chained alkyl groups as well as cyclo-alkyl groups. The term "lower alkyl", unless specifically stated otherwise, includes normal alkyl, branch chained alkyl as well as cyclo-alkyl groups having 1 to 6 carbon atoms.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

With reference to Formula 1, in the compounds which are preferably incorporated into the pharmaceutical compositions or formulations of the present invention, and which are used in the method of administering such formulations to animals and humans as $\alpha_2$ adrenergic agents, preferably the $R_3$, $R_4$ and $R_6$ groups are H. Preferably n is zero, and in that case the $R_1$ and $R_2$ groups preferably both are independently from one another, lower alkyl having 1 to 3 carbons. Compounds are also preferred where one of the $R_1$ and $R_2$ groups is lower alkyl, and the other is H. Active agents in the novel pharmaceutical compositions and in the novel method of administration of the present invention are also preferred where, in accordance with Formula 1, n is 2 and the $R_1$ and $R_2$ groups both are $CH_2$, there is no $R_5$ substituent and $R_6$ is H. Preferably, the active compounds in the composition and method of administration of the present invention are oxazoline and imidazoline derivatives; i.e. preferably in Formula 1 X is O or NH.

Most preferred as active agents in the novel compositions and methods of administration of the present invention are oxazoline or imidazoline compounds where: $R_3$ and $R_4$ are both H, and (1) n is 0 and $R_1$ and $R_2$ both are $CH_3$, or at least one the $R_1$ and $R_2$ groups is $CH_3$ and the other is H; or (2) n is 2 and $R_1$ and $R_2$ both are $CH_2$, there is no $R_5$ substituent and $R_6$ is H. The compounds which are most preferred as active ingredients in the composition and method of administration of the present invention, in accordance with the foregoing, are illustrated in Formula 2:

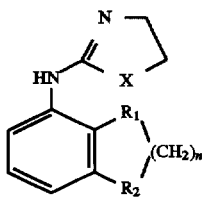

Formula 2

Compound 1 X=O n=0, $R_1$=$R_2$=$CH_3$,
Compound 1a X=O n=0, $R_1$=$CH_3$, $R_2$=H,
Compound 2 X=O n=2, $R_1$=$R_2$=$CH_2$,
Compound 3 X=NH n=0, $R_1$=$R_2$=$CH_3$,
Compound 3a X=NH n=0, $R_1$=$CH_3$, $R_2$=H, and
Compound 4 X=NH n=2, $R_1$=$R_2$=$CH_2$.

The present compounds are useful to provide one or more desired therapeutic effects in a mammal, as noted above. Among the desired therapeutic effects are an alteration, preferably a decrease, in the rate of fluid transport in the gastrointestinal tract of a mammal (anti-diarrhea effect), and an increase in the renal fluid flow in at least one kidney of a mammal (diuretic effect), in addition to the other affects which are generally recognized in the art to be caused by $\alpha_2$ adrenergic compounds. Thus, for example, the present compounds are effective as anti-diarrhea agents, and/or a medication for use in the treatment or management of kidney disease, as anti-spastic, anti-hypertensive, anti-ischemic, anti-epileptic, memory-enhancing agents and as sleeping aids.

Any suitable method of administering the present compound or compounds to the mammal to be treated may be used. The particular method of administration chosen is preferably one which allows the present compound or compounds to have the desired therapeutic effect in an effective manner, e.g., low medication concentration and low incidence of side effects. In many applications, the present compound or compounds are administered to a mammal in a manner substantially similar to that used to administer other alpha agonists, in particular $\alpha_2$ agonists, to obtain the same or a similar therapeutic effect.

The present compound or compounds may be included in a medication composition together with one or more other components to provide a medication composition which can be effectively administered. Such other components, e.g., carriers, anti-oxidants, bulking agents and the like, may be chosen from those materials which are conventional and well known in the art, e.g., as being included in medication compositions with $\alpha_2$ agonists. Whereas the effective dose of the compounds of the present compositions will depend on the nature of the host mammal and the specific diesease or condition treated it is anticipated that an effective daily dose of the compounds is in the range of 1 microgramm—10 mg per kg/body weight of the host. The ability of the compounds within the present invention to bind strongly and selectively to $\alpha_2$ adrenergic receptors in preference over $\alpha_1$ adrenergic receptors was confirmed by the following assay procedures which are generally recognized in the art to provide pertinent information with respect to the adrenergic activity of the compounds assayed: alpha$_1$ (human brain) assay, alpha$_2$A (HT-29 cells) assay, and alpha$_2$B (rat kidney) assay. A description of these assay procedures is as follows.

Receptor Binding Assays

Membrane preparation: Membrane suspensions were prepared from human cerebral cortex (HCC), HT-29 cells (HT) and rat kidney cortex (RtKC), as applicable. Tissues were homogenized in iced-cold buffer [250 mM sucrose, 5 mM tris, pH 7.4 (RtKC), or 50 mM Tris-HCl, 5 mM EDTA, pH 7.4 (HCC, HT)] with a Polytron homogenizer for 30 secs at setting #7, and centrifuged for 10 minutes at 300×g at 4° C. The supernatant was diluted 1:2 with 50 mM Tris-HCl buffer, pH 7.4 (RkCC, HCC) or pH 8.0 (HT) then centrifuged at 49,000×g for 15–20 minutes. The pellet fraction was washed 3 times (resuspended in Tris-HCl buffer and centrifuged for 15–20 minutes at 49,000×g). The pellet was then stored at −80° C. until the binding assay. Binding studies: The radioligands [$^3$H] rauwolscine (specific activity 80 Ci/mmol) and [$^3$H] prazosin (specific activity 77 Ci/mmol) were obtained from New England Nuclear, Boston, Mass. Frozen membrane pellet was resuspended in glycine glycine buffer, pH 7.6. Membrane protein homogenate (150–300 µg) was incubated with radioligand under the following conditions: 22° C., 30 minutes (HCC, HT), 0° C., 120 minutes (RtKC), in a final volume of 500 µl. At the end of the incubation period, the samples were filtered through glass fiber filters (Whatman GF/B) in a 96-well cell harvester and rapidly washed four times with 4 mls of iced-cold 50 mM Tris-HCl buffer. The filters were then oven dried and transferred to scintillation vials containing 5 mls of Beckman's Ready Protein[R] scintillation cocktail for counting. Non-specific binding was defined by 10 µM phentolamine. Protein concentrations were determined with a protein assay kit from Bio Rad. Binding isotherms, equilibrium dissociation and affinity constants were analyzed and determined by the non-linear least squares curve fitting program AccuFit Competition/Saturation by Beckman.

As it will be recognized by those skilled in the art from the forogoing descriptions, the described assays are radioligand assays which measure the binding of the test compound to the respective $\alpha_1$ or $\alpha_2$ receptor. The $K_i$ value which is calculated from these tests is called the "affinity constant" and is related to the concentration (expressed in nanomolar) of the test compound which displaces 50% of the radioligand from the receptors.

The results of these assays with examplary compounds within the scope of the invention are shown in the following Table where the column "$\alpha_1 Ki$" refers to $K_i$ values (in nanomolar) obtained in the Alpha$_1$ (human brain) Assay, the column "$\alpha_2 AKi$" refers to $K_i$ values obtained in the Alpha$_2$A (HT-29 cells) Assay, and the column "$\alpha_2 BKi$" refers to $K_i$ values obtained in the Alpha$_2$B (rat kidney) Assay.

TABLE

| Compound # | $\alpha_1 K_i$ | $\alpha_2 A K_i$ | $\alpha_2 B K_i$ |
|---|---|---|---|
| 1 | 1,211 | 5.1 | 8.5 |
| 1a | 7,401 | 35.7 | 208.4 |
| 2 | 1,629 | 2.2 | 6.2 |
| 3 | 434 | 5.8 | 1.5 |
| 3a | 2,171 | 7.5 | 25.3 |

As is well known in the art, in the foregoing assays a $K_i$ value which is approximately 100 nanomolar or less indicates that the compound is active. A compound which has a $K_i$ value of 10 or less is considered very active. In accordance with these criteria, the compounds used in accordance with the present invention are not active on the $\alpha_1$ adrenergic receptors, but are active on the $\alpha_2$ adrenergic receptors, and therefore can be considered specific (or highly selective) to the $\alpha_2$ adrenergic receptors.

Specific Embodiments

The compounds which were found in accordance with the present invention to be active $\alpha_2$ adrenergic agents can be made by a number of different synthetic chemical pathways. To illustrate the invention, there is here outlined a series of steps which have been proven to provide the active compounds of Formula 1, when such synthesis is followed in fact and in spirit. The synthetic chemist will readily appreciate that the specific conditions set out here can be generalized to any and all of the compounds represented by Formula 1. Furthermore, the synthetic chemist will readily appreciate that the herein described synthetic steps may be varied and or adjusted by those skilled in the art, to obtain the active compounds used in the novel pharmaceutical composition and method of administration of the present invention.

Active oxazoline compounds (in Formula 1 X=O) used in the pharmaceutical compositions and methods of administration of the present invention, where n=0 and where $R_1$ is lower alkyl of 1 to 6 carbons, $R_2$ is H or lower alkyl of 1 to 6 carbons, and where $R_3$ and $R_4$ are defined as above in connection with Formula 1, can be synthesized in accordance with the generalized procedure shown in Reaction Scheme 1.

As a first step of this reaction sequence, an aniline derivative corresponding to Formula 3 (where $R_1$ is lower alkyl of 1 to 6 carbons, $R_2$ is H or lower alkyl of 1 to 6 carbons, and where $R_3$ and $R_4$ are defined as in connection with Formula 1) is reacted with chloroethylisocyanate (Compound 5, a commercially readily available reagent). The reaction between compounds of Formula 3 and chloroethylisocyanate (Compound 5) is typically conducted in a neutral solvent, such as tetrahydrofuran (THF) and may be conducted at room temperature or at elevated temperature. In the event the aniline derivative (compound of Formula 3) is added to the reaction as a hydrochloride (or like) salt, an acid acceptor (such as triethylamine) may also be added to the reaction mixture.

REACTION SCHEME 1

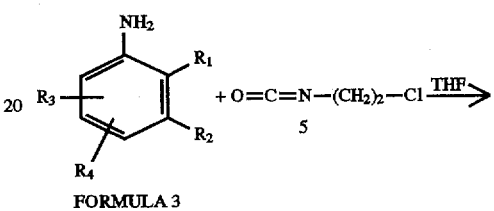

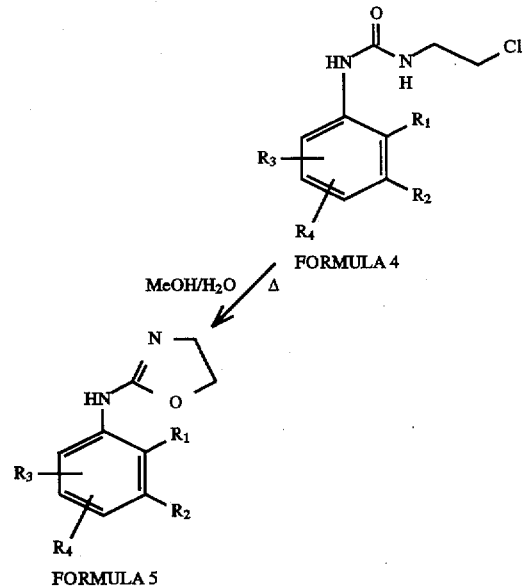

The reaction between chloroethylisocyanate (Compound 5) and the aniline derivative of Formula 3 provides the intermediate chloroethylurea derivative, compound of Formula 4 ($R_1$ is lower alkyl of 1 to 6 carbons, $R_2$ is H or lower alkyl of 1 to 6 carbons, and where $R_3$ and $R_4$ are defined as above in connection with Formula 1). The chloroethylurea derivative (Formula 4) typically precipitates out of the reaction mixture, and is isolated, for example by vacuum filtration. Generally speaking, the chloroethylurea derivative (Formula 4) can be adequately characterized and used in the next reaction without further purification.

The chloroethylurea derivative (Formula 4) is cyclized to provide the desired 2-(alkylphenylamino) oxazolines (Formula 5) by heating, preferably in an aqueous medium, such as a solvent mixture containing water and a lower alkohol, preferably methanol. Typically, the desired 2-(alkylphenylamino) oxazoline (Formula 5) obtained in the cyclization reaction, is isolated from the reaction mixture by first concentrating the same to remove the solvents, and thereafter by extraction in halogenated organic solvent (such as methylene chloride) followed by evaporation of the organic solvent. The desired product may also be recrystallized to attain further purity. The desired 2-(alkylphenylamino) oxazolines (Formula 5) may also be isolated from the cyclization reaction as the corresponding hydrochloride (or other) salt. For preparation of 2-(alkylphenylamino) oxazolines in general, and of Compound 1 in particular, further reference is made to U.S. Pat. No. 3,453,284, the specification of which is expressly incorporated herein by reference.

REACTION SCHEME 2

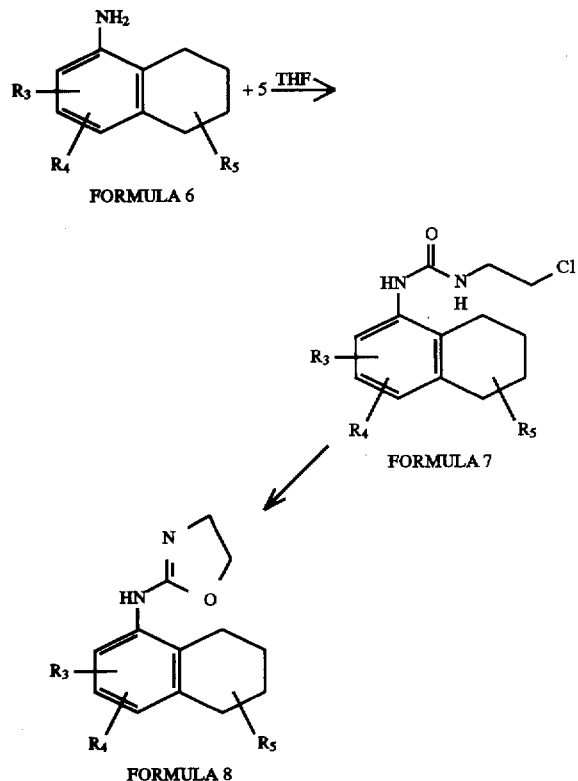

FORMULA 6

FORMULA 7

FORMULA 8

REACTION SCHEME 2

2-(5,6,7,8-Tetrahydronaphtylamino)-oxazoline derivatives (in Formula 1 X=O n=2), which in accordance with the present invention are active $\alpha_2$ adrenergic agents in mammals, can be made from the corresponding 5,6,7,8-tetrahydronaphtyl-1-amine, or substituted 5,6,7,8-tetrahydronaphtyl-1-amine, (compounds of Formula 6) by reaction with chloroethylisocyanate (Compound 5) as illustrated in Reaction Scheme 2. The conditions of this reaction are substantially similar to the analogous reaction described above with reference to Reaction Scheme 1. The resulting chloroethylurea intermediates (compounds of Formula 7) are cyclized into the desired 2-(5,6,7,8-tetrahydronaphtylamino)-oxazoline derivatives (Formula 8) by heating in a polar solvent, such as aqueous methanol. In Formulas 6, 7 and 8 the symbols $R_3$, $R_4$ and $R_5$ are defined as in connection with Formula 1. For preparation of 2-(5,6,7,8-tetrahydronaphtylamino)oxazoline derivatives in general, and of Compound 2 in particular, further reference is made to U.S. Pat. No. 3,432,600, the specification of which is expressly incorporated herein by reference.

REACTION SCHEME 3

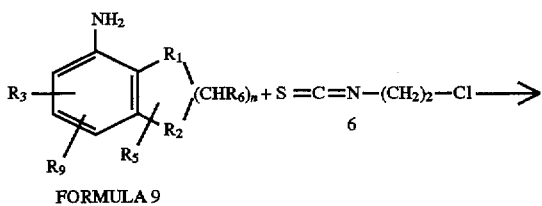

FORMULA 9

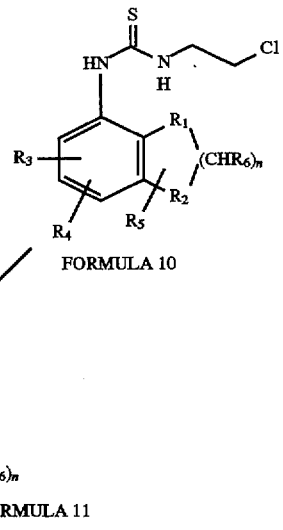

FORMULA 10

FORMULA 11

SCHEME 3

2-(2-Alkylphenyl-amino)-thiazolines (i. e. compounds where in Formula 1 X=S) which are active in accordance with the present invention as $\alpha_2$ adrenergic agents in mammals, can be synthesized in a reaction sequence which is analogous to the reaction sequences outlined above for the corresponding oxazoline derivatives; the only significant difference being that in the first step of the sequence chloroethylisothiocyanate (Compound 6) is used (instead of chloroethylisocyanate, Compound 5). Thus, referring to generalized Reaction Scheme 3, an alkyl substituted aniline corresponding to Formula 9 is reacted with chloroethylisothiocyanate (Compound 6) in a suitable solvent, (such as tetrahydrofuran) to provide the intermediate chloroethylthiourea (Formula 10). The symbols n and $R_1$ through $R_6$ in the formulas illustrated in Reaction Scheme 3 are defined as above with reference to Formula 1. In this connection it is noted that Formula 9 embraces substituted and unsubstituted 5,6,7,8-tetrahydro-1-naphtylamines, and that, in this specification with reference to the aromatic moiety of the active compounds used in the invention, the terms an "alkyl substituted phenyl" or "alkyl substituted aniline" broadly cover 5,6,7,8-tetrahydronaphtyl derivatives as well. Referring still to Reaction Scheme 3 the intermediate chloroethylthiourea (Formula 10) is cyclized, typically in an aqueous solvent mixture (e. g. $H_2O$ and $CH_3OH$) at room temperature or by gentle heating, to provide the desired 2-(2-alkylphenyl-amino)-thiazolines (Formula 11).

2-(2-Alkylphenyl-imino)-imidazolidines (i. e. compounds of Formula 1 where X=NH) which have been discovered in the present invention to be active as $\alpha_2$ adrenergic agents in mammals, can be synthesized, generally speaking, by the reaction of imidazoline-2-sulfonic acid (Compound 7) with an appropriately substituted aniline. Imidazoline-2-sulfonic acid (Compound 7) can be made in accordance with the procedure described in the chemical literature, (e. g. U.S. Pat. No. 4,656,291) from 2-imidazolidinethione (Compound 8). The synthetic steps leading to 2-(5,6,7,8-tetrahydro-1-naphtylimino)-imidazolidines [2-(5,6,7,8-tetrahydro-1-naphtylamino)-imidazolines] and to 2-(alkylphenylimino)-imidazolidines [2-(alkylphenylamino)-imidazolines], respectively, are illustrated in generalized Reaction Schemes 4 and 5.

REACTION SCHEME 4

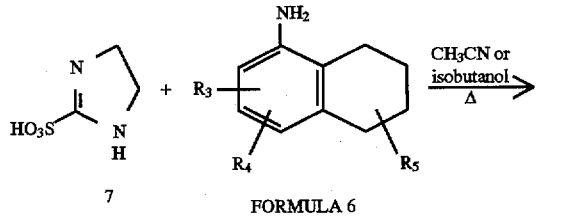

FORMULA 6

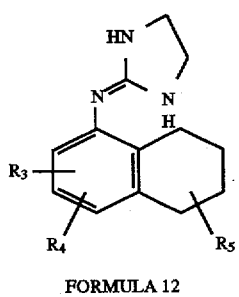

FORMULA 12

Thus, with specific reference to Reaction Scheme 4, imidazoline-2-sulfonic acid (Compound 7) is heated under pressure in a solvent (e. g. acetonitrile) with a substituted or unsubstituted 5,6,7,8-tetrahydronaphtyl- 1-amine (Formula 6), to provide the 2-(5,6,7,8-tetrahydro-1-naphtylimino)-imidazolidine derivatives of Formula 12. The symbols $R_3$, $R_4$ and $R_5$ in Formula 12 are defined the same as in Formula 6.

REACTION SCHEME 5

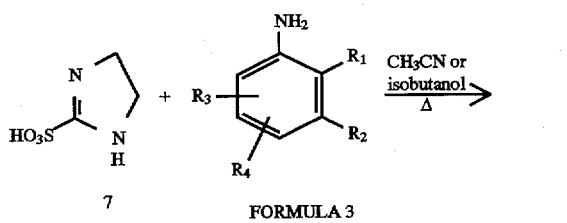

FORMULA 3

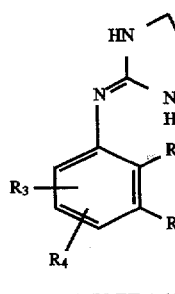

FORMULA 13

Reaction Scheme 5 illustrates the synthesis of 2-(alkylphenylimino)-imidazolidine derivatives (Formula 13) where, with reference to Formula 1 X=NH and n=0. In this synthesis a substituted aniline of Formula 3 is heated under pressure with imidazoline-2-sulfonic acid (Compound 7). In Formula 13 the symbols $R_1$, $R_2$, $R_3$ and $R_4$ are defined as in connection with Formula 3. For further description of the synthesis of compounds of Formula 13, reference is made to U.S. Pat. No. 4,515,800, the specification of which is expressly incorporated herein.

SPECIFIC EXAMPLES

2-[2,3-Dimethylphenylamino)-oxazoline (Compound 1)

Chloroethylisocyanate (Compound 5, Aldrich, 346 mg, 3.3 mmol) was added to a stirred solution of 2,3-dimethylaniline (Aldrich, 400 mg, 3.3 mmol) in tetrahydrofuran (5 ml) at room temperature. After 30 minutes a white precipitate formed. The solid chloroethylurea was collected by vacuum filtration yield: 477 mg (64%): mp 145°–146° C. HNMR (300 MHz, CDCl$_3$) σ 7.00 (m, 3H); 6.72 (br, 1H); 5.19 (br, 1H), 3.59 (m, 2H); 3.49 (m, 2H); 2.30 (s, 3H); 2.18 (s, 3H); Mass spectrum m/e 226.0872 ($C_1H_{15}ClN_2O$ requires 226.0872). The chlorethylurea (199 mg, 0.88 mmol) was suspended in $H_2O$ (4 ml) and $CH_3$ OH (4 ml) and heated to reflux for 1 hour. The reaction mixture was cooled to room temperature and concentrated in vacuo. The residue was dissolved in $CH_2Cl_2$ and washed with 1N NaOH (to pH 13). The organic layer was dried over $Na_2CO_3$ and concentrated in vacuo to yield 140 mg (84%) of the title compound as a white crystalline solid: mp 112°–113.5° C.; $^1$H NMR (300 MHz, CDCl$_3$) σ 7.19 (m, 1H); 7.09 (m, 1H), 6.91 (m, 1H); 5.00 (br, s, 1H); 4.40 (t, 2H); 3.70 (t, 2H); 2.30 (s, 3H); 2.15 (s, 3H); Mass spectrum m/e 190.1104 ($C_{11}H_{14}N_2O$ requires 190.1106).

2-α$_2$-methylphenylamino)-oxazoline (Compound 1a)

Chloroethylisocyanate (Compound 5, Aldrich, 440 mg, 4.2, mmol, 356 μl) was added dropwise to a stirred cold (0°) solution of ortho toluidine 500 mg, 4.66 mmol, 496 μl) in tetrahydrofuran (5 ml). After 15 minutes the reaction mixture was allowed to warm to room temperature. After one hour at room temperature a precipitate (solid chloroethylurea) was collected by filtration and washed with cold tetrahydrofuran.

Yield: 872 mg (98%).

The chloroethylurea (202 mg, 0.95 mmol) was dissolved in a mixture of methanol (7 ml) and water (5 ml) and the solution was refluxed for 4 hours. Then brine solution (2 ml) was added and the reaction mixture was extracted with diethyl ether. The reaction mixture was thereafter made basic to ph 14 by addition of 2.5N sodium hydroxide solution, and was extracted with ethyl acetate. The ethyl acetate layer was dried ($K_2CO_3$) and evaporated to dryness to yield the title compound, as a white solid (173 mg, approx 100%). Also see U.S. Pat. No. 3,453,284.

Following a substantially similar procedure and starting with the corresponding substituted aniline, the following additional examples of compounds of the invention can be synthesized, and utilized in the novel adrenergic compositions and methods of administration of the present invention:

2-(2,3-diethylphenylamino)-oxazoline;

2-(2-methyl-3-ethylphenylamino)-oxazoline;

2-(2-ethyl-3-methylphenylamino)-oxazoline;

2-(2,3,4-trimethylphenylamino)-oxazoline;

2-(2,3,5-trimethylphenylamino)-oxazoline;

2-(2,5,6-trimethylphenylamino)-oxazoline;

2-(5,6,7,8-tetrahydronaphthylamino)-oxazoline (Compound 2)

Chloroethylisocyanate (Compound 5 210 mg, 2.05 mmol) was added to a stirred solution at 5,6,7,8-tetrahydro-1- naphthylamine (302 mg, 2.05 mmol) in tetrahydrofuran (2 ml). After 30 minutes the resulting chloroethylurea was collected by vacuum filtration. Yield: 302 mg (58%) of fine white crystals: mp 101°–103°; H NMR (300 MHz, CDCl$_3$) σ 6.98–7.30 (m, 3H); 6.08 (brs, 1H); 5.19 (br, s, 1H); 3.68 (m, 2H); 3.55 (m, 2H); 2.79 (m, 2H); 2.61 (m, 2H); 1.80 (m, 4H); Mass spectrum m/e 252.1034 ($C_{13}H_{17}ClN_2O$ requires 252.1029). The chloroethyl urea (237 mg, 0.94 mmol) was suspended in $H_2O$ (3 ml) and $CH_3OH$ (3 ml) and heated to reflux for 18 hours. The reaction mixture was cooled to room temperature and worked up as above to yield after recrystallization (hexane/CHCl$_3$) 187.6 mg (87%) of the title compound: mp 160°–162° C.; $^1H$ NMR (300 MHz, CDCl$_3$) σ 7.23 (m, 1H); 7.08 (m, 1H); 6.75 (m, 1H); 5.55 (br, 1H); 4.35 (t, 2H); 3.70 (t, 2H); 2.70 (m, 2H); 2.58 (m, 2H); 1.80 (m, 4H); Mass spectrum m/e 216.1257 ($C_{13}H_{16}N_2O$ requires 216.1262).

Following a substantially similar procedure and starting with the corresponding substituted 5,6,7,8-tetrahydronaphtyl-1-amine, the following additional examples of compounds of the invention can be synthesized, and utilized in the novel adrenergic compositions and methods of administration of the present invention:

2-(2-methyl-5,6,7,8-tetrahydronaphthylamino)oxazoline;
2-(3-methyl-5,6,7,8-tetrahydronaphthylamino)oxazoline;
2-(4-methyl-5,6,7,8-tetrahydronaphthylamino)oxazoline;
2-(5-methyl-5,6,7,8-tetrahydronaphthylamino)oxazoline;
2-(6-methyl-5,6,7,8-tetrahydronaphthylamino)oxazoline;
2-(7-methyl-5,6,7,8-tetrahydronaphthylamino)oxazoline;
2-(8-methyl-5,6,7,8-tetrahydronaphthylamino)oxazoline;
2-(2-ethyl-5,6,7,8-tetrahydronaphthylamino)oxazoline;
2-(3-ethyl-5,6,7,8-tetrahydronaphthylamino)oxazoline;
2-(4-ethyl-5,6,7,8-tetrahydronaphthylamino)oxazoline;
2-(5-ethyl-5,6,7,8-tetrahydronaphthylamino)oxazoline;
2-(6-ethyl-5,6,7,8-tetrahydronaphthylamino)oxazoline;
2-(7-ethyl-5,6,7,8-tetrahydronaphthylamino)oxazoline;
2-(8-ethyl-5,6,7,8-tetrahydronaphthylamino)oxazoline;
2-(2,3-dimethyl-5,6,7,8-tetrahydronaphthylamino)oxazoline;
2-(2,4-dimethyl-5,6,7,8-tetrahydronaphthylamino)oxazoline;
2-(3,4-dimethyl-5,6,7,8-tetrahydronaphthylamino)oxazoline;
2-(2,5-dimethyl-5,6,7,8-tetrahydronaphthylamino)oxazoline;
2-(2,6-dimethyl-5,6,7,8-tetrahydronaphthylamino)oxazoline;
2-(2,7-dimethyl-5,6,7,8-tetrahydronaphthylamino)oxazoline;
2-(2,8-dimethyl-5,6,7,8-tetrahydronaphthylamino)oxazoline;
2-(3,5-dimethyl-5,6,7,8-tetrahydronaphthylamino)oxazoline;
2-(3,6-dimethyl-5,6,7,8-tetrahydronaphthylamino)oxazoline;
2-(3,7-dimethyl-5,6,7,8-tetrahydronaphthylamino)oxazoline, and
2-(3,8-dimethyl-5,6,7,8-tetrahydronaphthylamino)oxazoline.

2-(5,6,7,8-Tetrahydro-1-naphthylimino)-imidazolidine (Compound 4)

Preparation of imidazoline-2-sulfonic acid: 2-Imidazolidinethione (Compound 8, Aldrich, 66.3 g, 650 m/nol), $Na_2MoO_4$ (5 g, 227 mmol) and NaCl (15 g. 256 mmol) were added to 300 ml $H_2O$. Although some dissolution occurred, a solid residue remained in the liquid of the mixture. The mixture was cooled to −10° C. using an immersion cooler. 500 ml of a 30% (w/v) aqueous $H_2O_2$ solution was placed in a jacketed controlled drop rate addition funnel and cooled to 0° C. using an ice/$H_2O$ bath. The aqueous $H_2O_2$ solution was added to the mixture at a rate of 60 drops/min. The mixture was stirred for 16 hours at −10° C. During this time, the mixture changed from a white suspension to a dark blue solution to a light blue suspension. At the end of 16 hours, a solid was filtered from the suspension and dried in vacuo. No further purification was needed. Yield: 57.8 g (a yield of 52.3%) of the title compound as a white solid mp 157°–159° C.; H NMR (300 MHz, DMSO d$_6$) σ 10.38 (br, 2H); 3.85 (s, 4H). This solid was stable when stored in the dark at 0° C. for at least 6 months.

2-(5,6,7,8-tetrahydro-1-naphthylimino)-imidazolidine (Compound 4)

5,6,7,8-Tetrahydro-1-naphthylamine (Aldrich, 159 mg, 1.06 mmol), imidazoline-2-sulfonic acid (147.0 mg, 1.0 mmol, Compound 7 obtained as described above) and $CH_3CN$ (5 ml) were placed in a thick-walled cap which was sealed with a TEFLON™ screw and heated to 155° C. for 1.25 hours. The reaction mixture was cooled to room temperature and concentrated in vacuo. The resident was dissolved in CHCl$_3$ and washed with aq. 1N NaOH) to pH 13). The organic layer was separated, washed with brine, dried over $Na_2CO_3$ and concentrated in vacuo to yield a brown oil. The crude material was purified by flash chromatography (SiO$_2$; 80:20 CHCl$_3$/CH$_3$OH saturated with NH$_3$) to yield 29.5 mg (14%) of the title compound as a white solid: mp 138°–141° C.; H NMR (300 MHz, CDCl$_3$) σ 7.05 (t, 1H) 6.82 (m, 2H); 5.41 (br, 2H); 3.50 (s, 4H); 2.79 (m, 2H); 2.62 (m, 2H); 1.80 (m, 4H); Mass spectrum m/e 214.1339 ($C_{13}H_{16}N_3$ requires 214.1344).

Following a substantially similar procedure and starting with the corresponding substituted 5,6,7,8-tetrahydronaphtyl-1-amine, the following additional examples of compounds of the invention can be synthesized, and utilized in the novel adrenergic compositions and methods of administration of the present invention:

2-(2-methyl-5,6,7,8-tetrahydronaphthylimino)imidazolidine;
2-(3-methyl-5,6,7,8-tetrahydronaphthylimino)imidazolidine;
2-(4-methyl-5,6,7,8-tetrahydronaphthylimino)imidazolidine;
2-(5-methyl-5,6,7,8-tetrahydronaphthylimino)imidazolidine;
2-(6-methyl-5,6,7,8-tetrahydronaphthylimino)imidazolidine;
2-(7-methyl-5,6,7,8-tetrahydronaphthylimino)imidazolidine;
2-(8-methyl-5,6,7,8-tetrahydronaphthylimino)imidazolidine;
2-(2-ethyl-5,6,7,8-tetrahydronaphthylimino)imidazolidine;
2-(3-ethyl-5,6,7,8-tetrahydronaphthylimino)imidazolidine;
2-(4-ethyl-5,6,7,8-tetrahydronaphthylimino)imidazolidine;
2-(5-ethyl-5,6,7,8-tetrahydronaphthylimino)imidazolidine;
2-(6-ethyl-5,6,7,8-tetrahydronaphthylimino)imidazolidine;
2-(7-ethyl-5,6,7,8-tetrahydronaphthylimino)imidazolidine;
2-(8-ethyl-5,6,7,8-tetrahydronaphthylimino)imidazolidine;
2-(2,3-dimethyl-5,6,7,8-tetrahydronaphthylimino)imidazolidine;
2-(2,4-dimethyl-5,6,7,8-tetrahydronaphthylimino)imidazolidine;
2-(3,4-dimethyl-5,6,7,8-tetrahydronaphthylimino)imidazolidine;
2-(2,5-dimethyl-5,6,7,8-tetrahydronaphthylimino)imidazolidine;

2-(2,6-dimethyl-5,6,7,8-tetrahydronaphthylimino)
imidazolidine;

2-(2,7-dimethyl-5,6,7,8-tetrahydronaphthylimino)
imidazolidine;

2-(2,8-dimethyl-5,6,7,8-tetrahydronaphthylimino)
imidazolidine;

2-(3,5-dimethyl-5,6,7,8-tetrahydronaphthylimino)
imidazolidine;

2-(3,6-dimethyl-5,6,7,8-tetrahydronaphthylimino)
imidazolidine;

2-(3,7-dimethyl-5,6,7,8-tetrahydronaphthylimino)
imidazolidine; and 2-(3,8-dimethyl-5,6,7,8-tetrahydronaphthylimino)
imidazolidine.

2-(2,3-Dimethylphenylimino)-imidazolidine (Compound 3)

2,3 Dimethylaniline (Aldrich, 236 mg, 1.95 mmol), imidazoline-2-sulfonic acid (292 mg, 1.95 mmol, (Compound 7 obtained as described above) and $CH_3CN$ (4ml) were placed in a thick-walled glass tube and sealed with a TEFLON™ screw-cap. The reactants were heated to 155° C. for 6 hours. The reaction was worked up as described for Compound 4 and chromatographed ($SiO_2$; 70:30 $CHCl_3/CH_3OH$ saturated with $NH_3$) to yield a light yellow oil which was recrystallized (hexane/isopropanol to yield 61 mg (17%) of the title compound as an off-white crystalline solid: mp 141°–144° C.; H NMR (300 MHz, $CDCl_3$) σ 6.98 (m, 1H); 6.80 (m, 2H), 5.31 (br, 2H); 3.42 (s, 4H); 2.31 (s, 3H); 2.12 (s, 3H); Mass spectrum m/e 189.1259 ($C_{11}H_{15}N_3$ requires 189.1266). Alternatively, and preferably alcohols, most preferably isobutanol, are used instead of $CH_3CN$ in this reaction.

2-(2-methylphenylimino)-imidazolidine (Compound 3a);

Ortho toluidine (536 mg, 531 µl, 5 mmol) and imidazoline-2-sulfonic acid (750 mg, 5 mmol, (Compound 7 obtained as described above)) and $CH_3CN$ (6ml) were heated in a thick-walled glass tube at 150° C. for 16 hours. The reaction mixture was then cooled to 0° and made basic to pH 14 by addition of 2.5N NaOH solution. The mixture was extracted with methylene chloride, the combine extracts were died ($K_2CO_3$) and evaporated to dryness. Flash chromatography on silica gel yielded the title compound as a tan colored solid (47.0 mg, 5.37%).

Following a substantially similar procedure and starting with the corresponding substituted aniline, the following additional examples of compounds of the invention can be synthesized, and utilized in the novel adrenergic compositions and methods of administration of the present invention:

2-(2,3-diethylphenylimino)-imidazolidine;
2-(2-methyl-3-ethylphenylimino)-imidazolidine;
2-(2-ethyl-3-methylphenylimino)-imidazolidine;
2-(2,3,4-trimethylphenylimino)-imidazolidine;
2-(2,3,5-trimethylphenylimino)-imidazolidine;
2-(2,5,6-trimethylphenylimino)-imidazolidine.

What is claimed is:

1. A method of treating diseases or conditions of an animal of the mammalian species, the disease or condition being of the type which responds to treatment with alpha$_2$ adrenergic agents, the method of treatment comprising the steps of administering to the mammal a pharmaceutical composition which comprises as its active ingredient an effective amount of one or more compounds of the formula

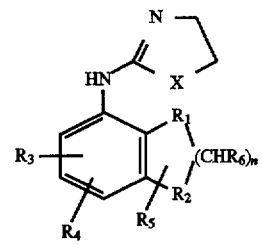

where

X is S;

n is an integer with the values of 0, 1 or 2;

$R_3$ and $R_4$ independently are H or lower alkyl having 1 to 6 carbons;

$R_6$ is H or lower alkyl of 1 to 6 carbons, with the proviso that when n is 0 then $R_1$ is lower alkyl having 1 to 6 carbon atoms and $R_2$ is H or lower alkyl having 1 to 6 carbon atoms, when n is 1 or 2, then $R_1$ and $R_2$ both are $CHR_5$, where $R_5$ independently is H or lower alkyl of 1 to 6 carbons, or salts of compounds of said formula.

2. The method of treatment of claim 1 wherein in the formula of the active ingredient n is zero.

3. The method of treatment of claim 1 wherein in the formula of the active ingredient n is 2.

4. A method of treating animals of the mammalian species, which are afflicted with a disease or condition of the type which is treated with an α$_2$ adrenergic agent having effect of altering the rate of fluid flow in the gastrointestinal tract, or anti-spastic, anti-hypertensive, anti-ischemic, anti-epileptic, anesthetic, memory-enhancing or sleep aiding effect, or the effect of increasing fluid flow in at least one kidney, the method of treatment comprising the steps of administering to the mammal a pharmaceutical composition which comprises as its active ingredient an effective amount of one or more compounds of the formula

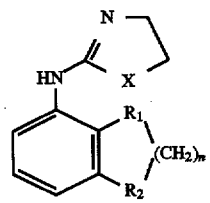

where

X is S;

n is an integer with the values of 0, 1 or 2, with the proviso that when n is 0 then $R_1$ is lower alkyl having 1 to 6 carbon atoms and $R_2$ is H or lower alkyl having 1 to 6 carbon atoms, when n is 1 or 2, then $R_1$ and $R_2$ both are $CH_2$, or salts of compounds of said formula.

5. The method of treatment of claim 4 wherein in the formula of the active ingredient n is zero.

6. The method of treatment of claim 4 wherein in the formula of the active ingredient n is 2.

* * * * *

UNITED STATES PATENT AND TRADEMARK OFFICE
CERTIFICATE OF CORRECTION

PATENT NO. : 5,708,015
DATED : January 13, 1998
INVENTOR(S) : Garst et al.

It is certified that error appears in the above-indentified patent and that said Letters Patent is hereby corrected as shown below:

Column 1, lines 30-31, "2. Brief Description of Background Art" should be a new heading.

Column 2, line 35, after "X is", delete ",".

Column 4, lines 55-56, "Binding Studies" should be a new heading.

Column 8, line 9, "$R_9$" should be --$R_4$--.

Column 10, line 10, "2-[" should be --2-(--.

Column 10, line 32, "2-$_2$" should be --2-(--.

Column 10, line 64, "2-(5,6,7,8-tetrahydronaphthylamino)-oxazoline" should be a new heading.

Column 11, line 64, "m/nol" should be --mmol--.

UNITED STATES PATENT AND TRADEMARK OFFICE
CERTIFICATE OF CORRECTION

PATENT NO. : 5,708,015
DATED : January 13, 1998
INVENTOR(S) : Garst et al.

It is certified that error appears in the above-indentified patent and that said Letters Patent is hereby corrected as shown below:

Column 1, line 55, "naphtylamino" should be --naphthylamino--.
Column 1, line 57, "antocholigeneric" should be --anticholigeneric--.
Column 3, line 43, after "one", add --of--.
Column 4, line 4, "genereally" should be --generally--.
Column 4, line 30, "diesease" should be --disease--.
Column 5, line 10, "forogoing" should be --foregoing--.
Column 6, line 65, "alkohol" should be --alcohol--.
Column 7, line 48, "Tetrahydronaphtylamino" should be --Tetrahydronaphthylamino--.
Column 7, line 52, "tetrahydronaphtyl" should be --tetrahydronaphthyl--.
Column 7, line 53, "tetrahydronaphtyl" should be --tetrahydronaphthyl--.
Column 7, line 60, "tetrahydronaphtylamino" should be --tetrahydronaphthylamino--.
Column 7, line 64, "tetrahydronaphtylamino" should be --tetrahydronaphthylamino--.
Column 8, line 52, "naphtylamines" should be --naphthylamines--.
Column 8, line 56, "tetrahydronaphtyl" should be --tetrahydronaphthyl--.

UNITED STATES PATENT AND TRADEMARK OFFICE
CERTIFICATE OF CORRECTION

PATENT NO. : 5,708,015
DATED : January 13, 1998
INVENTOR(S) : Garst et al.

It is certified that error appears in the above-indentified patent and that said Letters Patent is hereby corrected as shown below:

Column 9, line 5, "naphtylimino" should be --naphthylimino--.
Column 9, line 6, "naphtylamino" should be --naphthylimino--.
Column 9, line 36, "tetrahydronaphtyl" should be --tetrahydronaphthyl--.
Column 9, line 37, "naphtylimino" should be --naphthylimino--.
Column 10, line 20, "chlorethylurea" should be --chloroethylurea--.
Column 11, line 14, after "7.08 (m, 1H", add --)--.
Column 11, line 20, "tetrahydronaphtyl" should be --tetrahydronaphthyl--.
Column 12, line 35, "tetrahydronaphtyl" should be --tetrahydronaphthyl--.
Column 13, line 41, "died" should be --dried--.
Column 14, line 30, after "having", add --the--.

Signed and Sealed this

Sixteenth Day of June, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,708,015
DATED : January 13, 1998
INVENTOR(S) : Garst et al

It is certified that error appears in the above-indentified patent and that said Letters Patent is hereby corrected as shown below:

On the title page, item [75],
Delete "James E. Burke" and insert in place thereof
--James A. Burke--

Signed and Sealed this

Nineteenth Day of January, 1999

Attest:

Attesting Officer

*Acting Commissioner of Patents and Trademarks*